United States Patent [19]

Melzig

[11] Patent Number: 5,399,687

[45] Date of Patent: Mar. 21, 1995

[54] PHOTOCHROME ALKYL SUBSTITUTED SPIROINDOLINE COMPOUNDS

[75] Inventor: Manfred Melzig, Wessling, Germany

[73] Assignee: Optische Werke G. Rodenstock, Munich, Germany

[21] Appl. No.: 166,915

[22] Filed: Dec. 15, 1993

Related U.S. Application Data

[63] Continuation of Ser. No. 33,467, Mar. 18, 1993, abandoned, which is a continuation of Ser. No. 913,979, Jul. 16, 1992, abandoned, which is a continuation of Ser. No. 799,890, Dec. 2, 1991, abandoned, which is a continuation of Ser. No. 613,957, Nov. 15, 1990, abandoned, which is a continuation of Ser. No. 506,996, Apr. 10, 1990, abandoned, which is a continuation of Ser. No. 397,622, Aug. 24, 1989, abandoned, which is a continuation of Ser. No. 296,887, Jan. 12, 1989, abandoned, which is a continuation of Ser. No. 41,104, Mar. 19, 1987, abandoned.

[30] Foreign Application Priority Data

Jul. 19, 1985 [DE] Germany ............. 35 25 891.8

[51] Int. Cl.$^6$ ............. C07D 498/10; C07D 498/20
[52] U.S. Cl. ............. 544/71
[58] Field of Search ............. 544/71

[56] References Cited

U.S. PATENT DOCUMENTS

| 4,634,767 | 1/1987 | Hoelscher et al. ............. 544/71 |
| 4,637,698 | 1/1987 | Kwak et al. ............. 544/71 X |
| 5,017,698 | 5/1991 | Machida et al. ............. 544/71 |

FOREIGN PATENT DOCUMENTS

| 141407 | 5/1985 | European Pat. Off. |
| 1927849 | 12/1970 | Germany |

Primary Examiner—Richard L. Raymond
Attorney, Agent, or Firm—Antonelli, Terry, Stout & Kraus

[57] ABSTRACT

A compound is described with the general formula

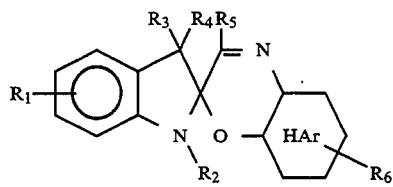

where
$R^1$ is one to four substituted groups from the series —Z, —OZ, —NZ$_2$, —NHZ, NH$_2$, CN, CF$_3$ with Z: C$_1$-C$_5$ alkyl, phenyl, pyridyl, benzyl
$R_2$ = —H, —Z, —CH$_2$Z,
$R_3, R_4, R_5$ = —NH$_2$, —NHZ, —NZ$_2$, —OZ, —Z, —H
$R_6$ = —H, —Z, —OZ, —CN, —NO$_2$
HAr = heteroaromatic substances with two or three cores and with 1 or 2N atoms in accordance with one of the following structural formulae:

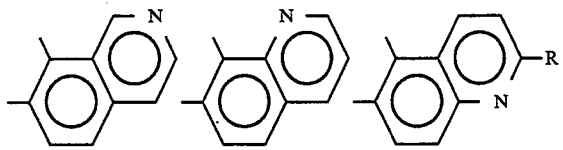

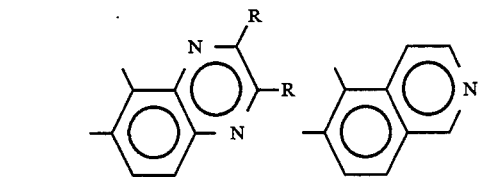

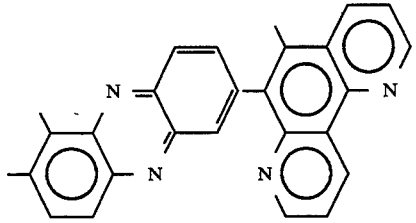

(Abstract continued on next page.)

Abstract -continued
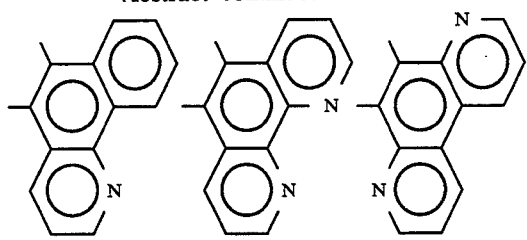
The compounds in accordance with this invention have the advantage that their migration in plastic materials usually used for spectacle lenses is lower so that no softening agent effect occurs which would be of a disadvantage for the coating of such lenses with, for example, anti-reflection coating layers.
20 Claims, No Drawings

PHOTOCHROME ALKYL SUBSTITUTED SPIROINDOLINE COMPOUNDS

This application is a continuation of application Ser. No. 033,467, filed on Mar. 18, 1993, (now abandoned), which is a continuation of application Ser. No. 913,979, filed on Jul. 16, 1992, (now abandoned), which is a continuation of application Ser. No. 799,890, filed on Dec. 2, 1991, (now abandoned), which is a continuation of application Ser. No. 613,957, filed on Nov. 15, 1990, (now abandoned), which is a continuation of application Ser. No. 506,996, filed on Apr. 10, 1990, (now abandoned), which is a continuation of application Ser. No. 397,622, filed on Aug. 24, 1989, (now abandoned), which is a continuation of application Ser. No. 296,887, filed on Jan. 12, 1989, (now abandoned), which is a continuation of application Ser. No. 041,104, filed on Mar. 19, 1987, (now abandoned).

DESCRIPTION

1. Technical Background

The invention relates to photochromic compounds, i.e. to substances whose absorption properties vary in accordance with the ambient light so that also the tint of materials dyed with these substances will vary in intensity and colour impression in accordance with the ambient light.

Photochromic substances may be used in a great variety of applications, for example they are used for the manufacture of photochromic sunglass lenses made from plastic, of spectacle frames, etc.

2. State of the Art

Photochromic substances are already known from, for example, the U.S. Pat. Nos. 3,562,172, 3,578,602, 4,215,010 or from the German disclosure DE-OS 29 26 266.

However, the photochromic substances or compounds known from these publications have, among others, the disadvantage that their photochromic effect is highly dependent on temperature: as the ambient temperatures increase, the amount of darkening becomes less when the degree of illumination remains constant.

For this reason, photochromic substances are proposed in WO 85/02619 whose general framework agrees with that of the substances described in the publications listed above but for which the temperature dependence of their photochromic effect has been reduced considerably by means of appropriate residues added to the framework.

However, the substances known from WO 85/02619 have, in part, the disadvantage that they show a slight blueish tint when not exposed to light radiation. This means that a spectacle lens tinted with these substances will also have a slight blueish tint in the non-illuminated state and the transmission $\tau(V\lambda)$ through this tint in a non-illuminated state may under certain circumstances be less than 85%, which is, for example, the value recommended for vehicle drivers for night driving.

With the similarly constructed 1,3,3-trimethylindoline-spirophenanthro-1.4-2H-oxazines known from the E. German patent DDR-PS 156 372, it is also only possible to manufacture lenses with a strong violet tint. In the phenanthrene system this is true even without the introduction of substituted groups. If drawing substituted groups (2- or 4-nitrophenanthrene) are introduced, then even stronger tints are produced in the non-illuminated state. Finally, 2, 7-d-nitroderivative is present in almost its full colour at a temperature as low as room temperature.

For this reason, photochromic substances are proposed in the European disclosure EU-OS 0141 407 which have a structure in accordance with the general formula given in claim 1. These photochromic substances are colourless in a non-stimulated state, i.e. they have practically no reducing effect on the transmission of, for example, a spectacle lens. However, a disadvantage of the photochromic compounds known from this publication is, that in the materials usually used for plastic spectacle lenses, such as, for example, diethylene-bis-allyl carbonate, they show a comparatively high tendency to migrate. This is a disadvantage in the AR-coating of spectacle lenses as the photochromic dyestuff molecules which migrate on the surface at increased temperature in a vacuum produce non-adhesive anti-reflection coatings.

REPRESENTATIVE OF THE INVENTION

The object of this invention is to disclose photochromic compounds which show only a low tendency towards migration so that vacuum-coated layers will show good adhesion and which will also show a relaively low tint and only a low dependence on temperature of the photochromic effect in a non-illuminated state.

A solution to this object can be found according to this invention with compounds of the general formula:

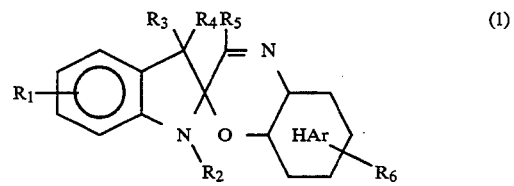

(1)

where
- $R_1$ = one to four substituted groups from the series —Z, —OZ, —NZ$_2$, —NHZ, —NH$_2$, —CN, —CF$_3$ with Z: $C_1$-$C_5$ alkyl, phenyl, pryridyl, benzyl
- $R_2$ = —H, —Z, —CH$_2$Z
- $R_3,R_4,R_5$ = —NH$_2$, NHZ, NZ$_2$, —OZ, —Z, —H
- $R_6$ = —H, —Z, —OZ, —CN, —NO$_2$
- HAr = heteroaromatic substances with two or three cores and with 1 or 2N atoms in accordance with one of the following structural formulae:

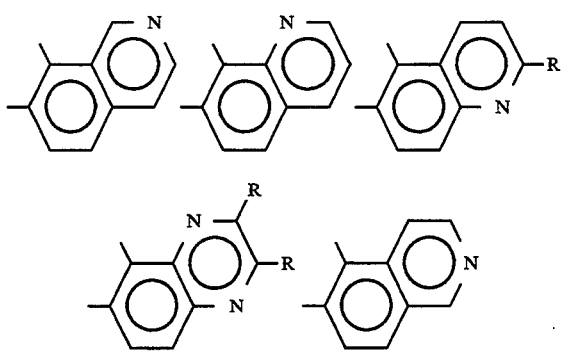

-continued

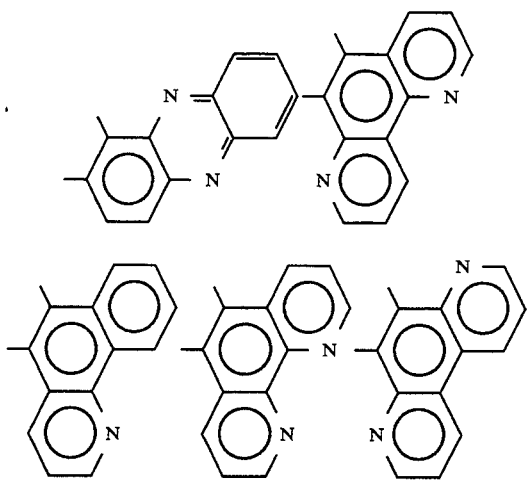

It has been recognised in accordance with this invention that the migration of the photochromic molecules can be reduced considerably if different heteroaromatic substances (HAr) to those described in EU-OS 0 141 407 are used. The heteroaromatic substances used according to this invention and particularly the preferred benzo or pyrido rings show considerable advantages over rather long C chains on the indoline nitrogen atom such as are used in accordance with EU-OS 0 141 407 as these comounds will give the photochromic molecule the properties of a softening agent.

As a result, the compounds proposed according to this invention have the advantage over the known molecules that their migration is lower so that plastic lenses treated with thee compounds can be anti-reflection coated without problems.

As already described in WO 85/02619, the residues $R_2$, $R_3$, $R_4$ and $R_5$ are decisive for the reduction of ther photochromic effect's dependence on temperature:

Under the effect of shortwave light the spiro-C-O bond opens; in this way the molecules shown below, which are in equilibrium with each other, are formed from the base form, i.e. from the molecule with the general formula (1):

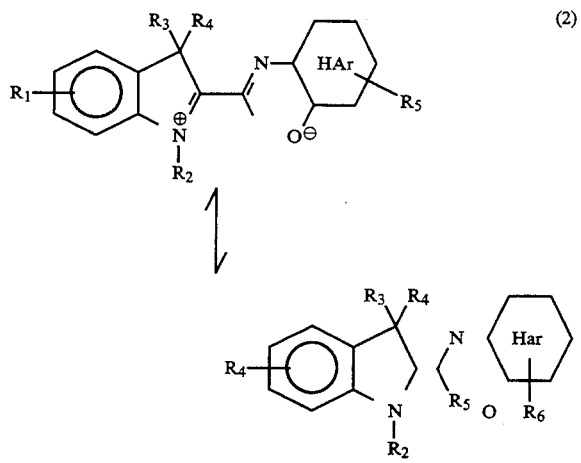

The molecules with the structural formula (2) have a blue colour while the molecule with the structural formula (1) is colourless.

Instead of a naphtaline residue as with the compounds known from WO 85/02619 or of a phenanthrene residue in accordance with DDR-PS 156 372, the compounds according to the present invention with the general formula (1) have a heteroaromatic substance with two or three cores and with 1 or 2N atoms (0 to 2N atoms per core). Due to this modification of the "frame" of the spiro compounds, which modification is not referred to in EU-OS 0141 407 and of which no mention is made of its advantages with regard to the migration properties in the State of the Art (see, for example, the solution attempt in a diferent direction for the molecules known from DDR-PS 156 372), an equilibrium is also obtained for molecules with low migration between the forms with the general formula (2) and the base form (1) which equilibrium in the non-illuminated state is closer to the base form which is colourless, so that the transmission of the compounds in accordance with the invention is still higher than with molecules with comparable migration properties.

With the newly proposed compounds with the general formula (1) the back reaction is also enhanced by increasing temperatures, i.e. the equilibrium between molecules with the structural forms (1) or (2) will be pushed away from the modification (2) towards the base form (1) with increasing temperature and constant illumination.

In this process, the residue $R_5$ represents a high steric (and also an electrical) hindrance to the back reaction. This is also true to a lesser extent for the residues $R_2$, $R_3$, and $R_4$.

In the same way as for the compounds described in WO 85/02619, the photochromic substances in accordance with this invention also have the additional advantage of positive thermochromaticity if the residues $R_3$ and $R_4$ are greater than methyl: Due to this positive thermochromaticity a darkening is produced with increasing temperature which is dependent on the illumination and which, in part, reverses the negative effect of the back reaction.

Further developments of the invention are given in the sub-claims.

In claims 2 and 3 some particularly to be preferred compounds are given which have the advantage that the heteroaromatic substances used can be synthesised according to known principles.

The modification claimed in claim 4, where a $CH_3$ residue is provided on the heteroaromatics core in an orthogonal position to the N atom, opens up the possibility of producing strongly coloured initial compounds by substituting, for example,

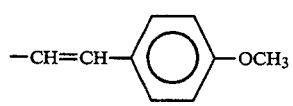

for the $CH_3$ residues by means of condensation with paramethoxybezaldehyde (claim 5). The colour of these new compounds will be, for example, orange to red in a non-illuminated state and so will provide a different colour change impression.

Below, compounds in accordance with the invention are shown in example form and compared with the state-of-the-art photochromic compounds:

The synthesis of the photochromic compound according to the invention is done in a known fashion by condensing a substituted 2-alkylene indoline

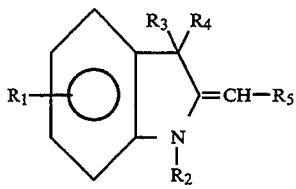

with an O-hydroxy-nitroso-heteromatic substance, for example with 7-hydroxy-8-nitroso-isochinoline:

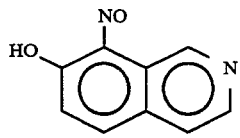

The formation of the 2-alkylene indoline can be done by synthesis beforehand or during the last synthesis step from a corresponding indoleninium salt. The introduction of the residue $R_5$ is also possible in this step via the condensation agent. As the principles of the reaction steps are known, it is not necessary to go into them in any detail here. Merely the final reaction step should be briefly mentioned:

An 0.01 mol o-hydroxy-nitroso-compound is suspended under stirring in 100 ml absolute ethanol in a 250 ml three-necked flask, which is equipped with a thermometer, a dropping funnel and a distilling bridge with reflux condenser and a water trap, and heated to boiling point. 5 ml benzol are added as a drag. 0.01 mol indoline base, dissolved in 50 ml absolute ethanol and with the addition of 0.9 ml piperidine, is dripped into the boiling mixture. The reaction mixture is kept at boiling point for two hours and subsequently the reaction water produced is separated off at the water trap.

The solvents are drawn out of the cooled solution in a vacuum. The dark-brown and often tarry residue is chromatographised on aluminium oxide with methylene chloride. The main fraction is vapourised in a vacuum for drying and then recrystallised from methanol.

If this crystallisation is carried out in the dark and at low temperatures, then a powder with an ash-yellow to brown colour is produced, with the exception of those cases where $R_2=R_3=C_2H_5$ and $R_2=C_2H_5$ and $R_3=C_3H_7$. In this cases the colour is green to dark green. When exposed to illumination the substances will usually become more or less green depending on the portion of molecules which go into the opened blue form (structual formula 2).

With the reaction steps described above, the following compounds (among others) have been produced:

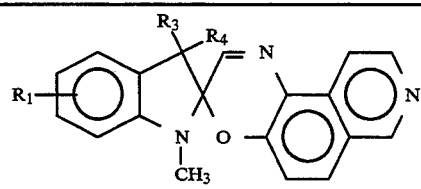

| No. | $R_1$ | $R_3, R_4$ | $R_5$ | |
|---|---|---|---|---|
| 1 | —H | —CH$_3$ | —H | 1,3,3-trimethyl-spiro(indoline-2,3' (3H̲)-pyrido(3,4-f)(1,4)benzoxazine) |
| 2 | —H | —C$_2$H$_5$ | —H | 3,3-diethyl-1-methyl-spiro(indoline-2-3'(3H̲)-pyrido(3,4-f)(1,4)benzoxazine) |
| 3 | -5-NH$_2$ | —CH$_3$ | —H | 5-amino-1,3,3-trimethyl-spiro(indoline-2,3'(3H̲)-pyrido(3,4-f)(1,4)benzoxazine) |

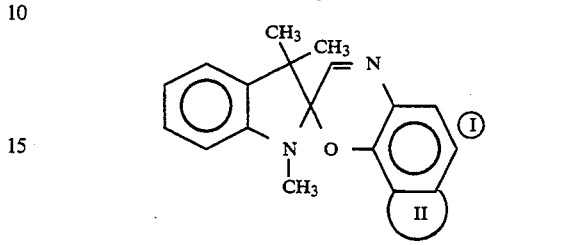

| No. | I | II | |
|---|---|---|---|
| 4 | H,H | Pyrido | 1,3,3-trimethyl-spiro(indoline-2,3' (3H̲)-pyrido(3,2-d)(1,4)benzoxazine) |
| 5 | Benzo | Pyrido | 1,3,3-trimethyl-spiro(indoline-2,3' (3H̲)-benzo(f)-pyrido(2,3-d)(1,4) benzoxazine |
| 6 | Pyrido | Pyrido | 1,3,3-trimethyl-spiro(indoline-2,3' (3H̲)-dipyrido(3,2-d:3,2-f)(1,4) benzoxazine |

In the following, the NMR data of the compounds 1 to 6 according to the invention are given. With the exception of compound 2, which was dissolved in acetone-d6, all compounds here were dissolved in CDCl$_3$.

| Compound | 1 | 2 | 3 | 4 | 5 | 6 |
|---|---|---|---|---|---|---|
| D, 1H | 9.1 | 9.1 | 9.1 | | | |
| M, 1H | 8.8 | 8.8 | 8.8 | | | 9.0 |
| M, 2H | | | | 8.7 | | |
| M, 3H | | | | | 9.1–8.6 | |
| M. 4H | | 1.85 | | | | |
| M, 6H | | | | | 7.7–6.2 | |
| M, 7H | | | 7.8–6.2 | | | |
| M, 8H | 7.9–6.2 | 8.0–6.4 | | 7.9–6.2 | | 8.0–6.2 |
| QD, 1H | | | | | | 9.4 |
| QS, 3H | | | | | 7.9 | |
| S-wide, 2H | | | 3.35 | | | |
| S, 3H | 2.75 | 2.60 | 2.70 | 2.80 | 2.75 | 2.80 |
| S, 6H | 1.35 | | 1.35 | 1.35 | 1.35 | 1.35 |
| T, 3H | | 0.70 | | | | |
| T, 3H | | 0.85 | | | | |

The compounds 1 to 6 show largely the same behaviour as regards the photochromic effect, particularly with regard to the transmission in a non-illuminated state, the thermochromaticity and the migration properties in plastic materials such as are used for spectacle lenses. For this reason, in the following only compound 1 is to be compared with state-of-the-art compounds such as are known from U.S. Pat. No. 4,215,010 and WO 85/02619.

In a non-illuminated state the state-of-the-art compounds observed have the general formula:

Where for
the compound
known from
U.S. Pat. No. 4 215 010

-continued

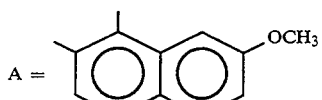

$R_3$, $R_4$ = $CH_3$, while for the compound known from WO 85/02619:

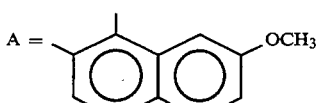

$R_3$, $R_4$ = $C_2H_5$

The following table gives the transmission $\tau_v(V\lambda)$ in a non-illuminated state at 15° C. as well as the temperature dependence of the optical density change $\Delta OD$ for a degree of illumination of 60,000 lux for the three compounds. In this example, the optical density is defined as $\Delta OD = \log \tau_o - \log \tau_s$, where $\tau_s$ is the transmission in an illuminated and $\tau_o$ the transmission in a non-illuminated state.

| $\tau_o(V\lambda)$<br>Temp (°C.) | Comp. 1<br>91%<br>$\Delta$ OD | U.S. Pat. No. 4215010<br>92%<br>$\Delta$ OD | WO 85/02619<br>85%<br>$\Delta$ OD |
|---|---|---|---|
| 5 | 0.718 | 0.964 | |
| 15 | 0.584 | 0.602 | |
| 23 | 0.432 | 0.273 | 0.475 |
| 30 | 0.262 | 0.172 | 0.291 |
| 40 | 0.128 | 0.077 | |

It can be seen from the table above that with practically identical photochromic performance at 15° C. the compound in accordance with this invention shows a lower darkening at lower temperatures than the compound known from U.S. Pat. No. 4,215,010 and a stronger darkening at higher temperatures.

In comparison with the compound known from WO 85/02619, the compound in accordance with the invention (comp. 1) shows a clearly greater transmission in a non-illuminated state while having practically the same temperature behaviour in darkening so that, for example, spectacle lenses dyed with the compounds according to this invention can also be worn for night-driving.

I claim:

1. A compound represented by the following graphic formula:

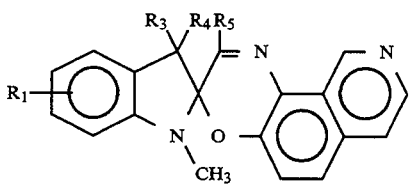

wherein
$R_1$ is H or —5—$NH_2$
$R_3$, $R_4$ are each $CH_3$ or $C_2H_5$
$R_5$ is H.

2. A compound represented by the following graphic formula:

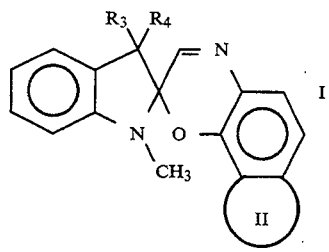

wherein
I: H, H or benzo or pyrido
II: pyrido wherein said pyrido are linked as pyrido (3,2-d), pyrido (2,3-d) or pyrido(3,4-f).

3. A compound represented by the following graphic formula:

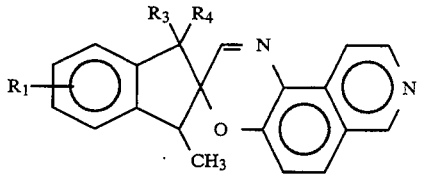

wherein $R_1$ is —H, —5—$NH_2$, or —$CH_3$; and
wherein $R_3$ and $R_4$ are the same or different groups selected from the group consisting of —$CH_3$ and —$C_2H_5$.

4. A compound represented by the following graphic formula:

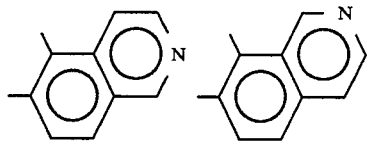

wherein
$R_1$ is one to four substituted groups from the series —Z, —OZ, —$NZ_2$, —NHZ, —$NH_2$, —CN, —$CF_3$; where Z is $C_1$–$C_5$ alkyl, phenyl, pyridyl, or benzyl;
$R_2$ is —H, —Z, —$CH_2$-pyridyl or $C_6$ alkyl;
$R_3$, $R_4$, $R_5$, is —H, —Z, —OZ, —NZ, —NHZ, —$NH_2$;
$R_6$ is —H, —Z, —OZ, —CN, —$NO_2$;
HAr represents heteroaromatic substances with two or three cores and with 1 or 2N atoms in accordance with one of the following structural formulae:

-continued

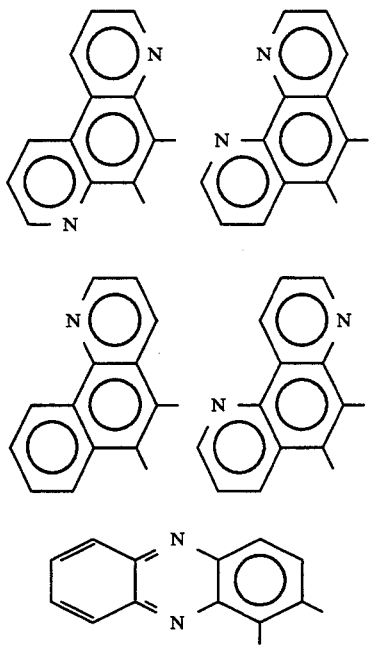

5. A compound according to claim 3, namely 1,3,3-trimethyl-spiroindoline-2,3'-3H-pyrido [3,4-f] (1,4) benzoxazine.

6. A compound according to claim 3, namely 3-ethyl-1, 3-dimethyl-spiroindoline-2,3'-3H-pyrido [3,4-f] (1,4) benzoxazine.

7. A compound according to claim 3, namely 3,3-diethyl-1-methyl-spiroindoline-2,3'-3H-pyrido [3,4-f] (1,4) benzoxazine.

8. A compound according to claim 3, namely 1,3,3,5-tetramethyl-spiroindoline-2,3'-3H-pyrido [3,4-f] (1,4) benzoxazine.

9. A compound according to claim 2, namely 1,3,3,6-tetramethyl-spiroindoline-2,3'-3H-pyrido [3,4-f] (1,4) benzoxazine.

10. A compound according to claim 4, namely 3-ethyl-1, 3,5-trimethyl-spiroindoline-2,3'-3H-pyrido [3,4-f] (1,4) benzoxazine.

11. A compound according to claim 4, namely 3-ethyl-1, 3,6-trimethyl-spiroindoline-2,3'-3H-pyrido [3,4-f] (1,4) benzoxazine.

12. A compound according to claim 4, namely 1,3,3,5,6-pentamethyl-spiroindoline-2,3'-3H-pyrido [3,4-f] (1,4) benzoxazine.

13. A compound according to claim 4, namely 3-ethyl-1, 3,5,6-tetramethyl-spiroindoline-2,3'-3H-pyrido [3,4-f] (1,4) benzoxazine.

14. A compound according to claim 2, namely 1,3,3-trimethyl-spiroindoline-2,3'-3H-benzo(f)-pyrido [2,3-d] (1,4) benzoxazine.

15. A compound according to claim 2, namely 1,3,3-trimethyl-spiroindoline-2,3'-3H-dipyrido [3,2-d:3,2-f] (1,4) benzoxazine.

16. A compound according to claim 4, namely 3-ethyl-1, 3,5,6-tetramethyl-spiroindoline-2,3'-3H-dipyrido [3,2-d: 3,2-f]-(1,4)benzoxazine.

17. A compound 1,3,3-trimethyl-spiroindoline-2,3'-3H-pyrido [2,3-f] (1,4) benzoxazine.

18. A compound 3-ethyl-1,3-dimethyl-spiroindoline-2,3'-3-pyrido [2,3-f] (1,4) benzoxazine.

19. A compound 3,3-diethyl-1-methyl-spiroindoline-2,3'-3H-pyrido [2,3-f] (1,4) benzoxazine.

20. A compound according to claim 4, namely 5-amino-1, 3,3-trimethyl-spiroindoline-2,3'-3H-pyrido [3,4-f] (1,4) benzoxazine.

* * * * *